United States Patent

Baldauf

[11] Patent Number: 5,924,430
[45] Date of Patent: Jul. 20, 1999

[54] TOOTHPICK

[76] Inventor: Hanspeter Baldauf, Konradstrasse 33, CH-8023 Zurich, Switzerland

[21] Appl. No.: 09/029,472
[22] PCT Filed: Jun. 18, 1996
[86] PCT No.: PCT/CH96/00232
  § 371 Date: Sep. 24, 1998
  § 102(e) Date: Sep. 24, 1998
[87] PCT Pub. No.: WO97/07749
  PCT Pub. Date: Mar. 6, 1997

[30] Foreign Application Priority Data

Aug. 30, 1995 [CH] Switzerland .............................. 2464/95

[51] Int. Cl.[6] ...................................................... A61C 15/00
[52] U.S. Cl. ............................................ 132/321; 132/329
[58] Field of Search ..................................... 132/321, 329, 132/308, 309, 323, 325; 401/6, 7, 8; 15/167.1, 227

[56] References Cited

U.S. PATENT DOCUMENTS

| | | | |
|---|---|---|---|
| 973,842 | 10/1910 | Baird | 132/321 |
| 2,623,003 | 12/1952 | Friedlob et al. | 132/321 |
| 5,213,428 | 5/1993 | Salman | 401/7 |

FOREIGN PATENT DOCUMENTS

| | | | |
|---|---|---|---|
| 423541 | 4/1991 | European Pat. Off. | 132/321 |
| 196070 | 5/1938 | Switzerland | 132/321 |
| 490034 | 10/1936 | United Kingdom | 132/321 |
| 9607367 | 3/1996 | WIPO | 132/321 |

*Primary Examiner*—Gene Mancene
*Assistant Examiner*—Pedro Philogene
*Attorney, Agent, or Firm*—Pauley Petersen Kinne & Fejer

[57] ABSTRACT

A toothpick made of biodegradable material composed of a thermoplastic, water-soluble and foodstuff-grade base material. The base material substantially consists of starch, glucose, gelatine, cellulose, collagen or their derivatives. Various active substances such as fragrances, dyes or pharmaceutical compositions may be added to the base material. The active substances may however also be added to the finished product, i.e. the toothpick, by coating the toothpick therewith.

16 Claims, No Drawings

TOOTHPICK

BACKGROUND OF THE INVENTION

1. Field of the Invention

This invention relates to a biodegradable toothpick.

2. Description of Prior Art

Toothpicks made of wood, or respectively of quills, have been known for decades and are commercially available. Such toothpicks are therefore made of a biodegradable material, but have various undesirable side effects. Wooden toothpicks can splinter or break and are often hygienically undesirable. If wood splinters enter between teeth during cleaning, they are hard to remove and hardly decompose, even over long periods of time. The danger of individual wood fibers or small wood splinters entering the gums during cleaning of the teeth is not inconceivable. Inflamed gums often result.

Toothpicks made of quills pose such dangers to a much smaller extent. However, one problem is that quills are a natural product and accordingly can be inconsistent. Quills often have sharp edges in particular and therefore lead to injury to the gums.

These problems have long been known, and accordingly various toothpicks made of other, particularly non-biodegradable materials, are also commercially available. Toothpicks made of plastic or metal, as well as metal-coated plastic toothpicks, are particularly known. All such toothpicks have the advantage that they appear to be extremely sanitary, can be technically reproduced and accordingly can have exact shapes, so that the danger of injury is virtually eliminated. But metal or metal-coated toothpicks in particular are relatively expensive and therefore are intended for repeated use, which does not conform to sanitary concepts.

A further problem is that toothpicks are often placed on the edge of a food plate after use and in this way get into the kitchen along with the remnants of the food, which is often used as animal feed. In this case such toothpicks can result in injury to the gums of animals.

Finally, toothpicks are sometimes also used in the preparation of food, for example for maintaining pieces of meat in a relative position to each other during preparation. Typical examples are thin, rolled-up pieces of meat which are fixed in this way, or the placement of a piece of bacon around a sausage. Toothpicks are also often used in the preparation of cordon bleu. With all these applications there also is the danger that the consumer places the hardly visible toothpick into his or her mouth and can become injured in this way. This is a particular problem for persons with artificial teeth, which will hardly notice this condition and therefore the toothpick can enter the throat.

DESCRIPTION OF THE INVENTION

It is therefore one object of this invention to make a conventional toothpick from a material which permits industrial production without the above mentioned disadvantages occurring.

This object is attained with a toothpick made of a biodegradable material produced from a basic material which can be thermoplastically processed, is water-soluble and approved for foodstuffs.

A toothpick produced from such a material has none of the above mentioned disadvantages. Although such a toothpick can also break and a large or small part can remain in the space between teeth, this poses no problems, since it will automatically dissolve after some time. Even if such a toothpick gets into the kitchen waste used as animal feed, this poses no problems, because either the toothpick is dissolved in the liquids present or is at least sufficiently softened so that injury to an animal is no longer possible.

Besides the avoidance of the mentioned disadvantages, however, it is also possible to achieve advantages which had not been noted up to now.

The most essential part of this invention is the use of a base material with the appropriate properties mentioned at the outset. Various base materials with the respective properties are already commercially available and are used for the most diverse applications. Most of the known base materials with the mentioned properties are derivatives of starch, glucose, gelatin, cellulose or collagen. However, the base material can also be prepared from mixtures of such materials on different bases. In the process it is only necessary to make sure that such mixtures require at least approximately the same processing conditions. Plastic materials should be mentioned, which are made on a gelatin basis and can be thermoplastically processed and are used for producing capsules for medicaments. Such base materials are produced, for example by the Warner-Lambert Company, and are commercially available under the trademark Capsugel™. Base materials on a starch base, which can be thermoplastically processed, are water-soluble and approved for foodstuffs, have been available since the early 1980s and are offered by various manufacturers. For example, Mitsubishi Rayon Company Ltd. sells various products made of natural, water-soluble polysaccharides. The products made from such base materials are known, for example, under the trademarks Soafil™ and Soaperl™. Here, products in a thermoplastically extruded as well as thermoplastically injection-molded form are commercially known. The American Maize Products Company also manufactures several products on the basis of cornstarch which are suitable for the above mentioned purposes. Novamont S.p.A. also produces a thermoplastically processable base material under the trademark MATER-BI™, which is suitable for extruding, injection molding and blowing. This base material can be processed in conventional machinery and meets the FDA requirements regarding foodstuff suitability. Buck Werke GmbH & Co. of Bad Reichenhall, Germany, also manufactures such base materials on a starch, glucose and cellulose basis. It is possible with all these materials to set the desired parameters regarding water-solubility and processability in accordance with the desired requirements.

With all base materials mentioned, the initial form is a polymeric granulate which can be thermoplastically processed. The fineness of this granulate can vary between powder-like grains up to large-grained granules.

It is possible in principle to add the most diverse additives to the base materials. Flavorings which are approved for foodstuffs are particularly possible for this. These flavorings can be natural flavors obtained from various herbs and medicinal plants. Mint, anise or balm in particular are to be considered here. Other types of flavorings are also possible. Typical kitchen herbs, such as salt, pepper, paprika, caraway, sage, etc. are also suitable as flavor additives.

Besides flavorings approved for foodstuffs, colorings approved for foodstuffs are also possible as additives to the base material. These colorings can be of natural as well as artificial origin. In connection with the addition of all these flavoring and colorings it is essential that the flavorings and colorings also are sufficiently temperature-resistant to be processed thermoplastically without a loss of quality. The latter is of course a particularly essential prerequisite if it is intended to add certain pharmaceutical preparations to the base material. It is known that toothpicks are chewed for some time after eating. It is accordingly possible to provide toothpicks with digestion-enhancing means or, for example, to add preparations which add to the production of saliva. If anti-bacterial and/or anti-inflammatory materials are added to the thermoplastically processable base material, these materials must withstand the occurring processing temperatures. The last mentioned additives are advantageous in regard to oral cleanliness.

While in connection with the above described embodiments the various active materials have always been added to the base material, it is also possible to coat the finished toothpicks made of the thermoplastically processable base material later with various active materials, flavorings, colorings and the like. This solution is particularly used in connection with those materials which are incompatible with the raw base materials or cannot withstand the processing temperatures during the thermoplastic molding. However, such materials often can be applied later in a dissolved form, for example by dipping the finished object into such a solution or by spraying the solution on the finished object. This method per se has already been realized in connection with wooden toothpicks, which has been mainly limited to flavorings. Both the admixture and the coating with solutions containing natural medicines or natural medicinal plants are of particular interest for this invention. A particularly unusual application is also considered to be the admixture of nicotine to the base material or the coating for obtaining toothpicks which are suitable for quitting smoking.

In order to delay the dissolving of the toothpick, the toothpick can have a coating which seals the toothpick and in this way delays the dissolving in water. Only after the coating has been dissolved does the actual dissolving, or respectively breakdown of the base material of the toothpick begin. Such coating substances are also known in the food industry.

In connection with this invention, thermoplastic processing is understood to be every type of processing, wherein the shaping is provided by changing the base material into a plastic phase under the effect of heat and wherein the base material is shaped into a toothpick form in this phase. Working processes such as injection molding, molding or extrusion are possible. If necessary, finishing can be performed after setting. Therefore the base material can be present in different shapes prior to thermoplastic processing, such as in the form of granules, a powder or a flowable mass.

I claim:

1. A toothpick made of a biodegradable material, the toothpick comprising: a base material which is thermoplastically processed, water-soluble and approved for foodstuffs, when molded the base material is converted to a ductile form by heating and is formed into a shape of the toothpick, and the toothpick being soluble in water in one of a finished coated state and a finished uncoated state.

2. The toothpick in accordance with claim 1, wherein the base material is selected from a group consisting of starch, glucose, gelatin, cellulose, collagen, and mixtures thereof.

3. The toothpick in accordance with claim 2, wherein prior to processing the base material is formed as granules of a polymer.

4. The toothpick in accordance with claim 2, wherein at least one of flavorings and colorings approved for foodstuffs is added to the base material.

5. The toothpick in accordance with claim 2, wherein a pharmaceutical material is added to the base material.

6. The toothpick in accordance with claim 2, wherein at least one of an anti-bacterial material an anti-inflammatory material is added to the base material.

7. The toothpick in accordance with claim 1, wherein the base material is coated.

8. The toothpick in accordance with claim 7, wherein the coating consists of a substance which delays dissolving in water.

9. The toothpick in accordance with claim 7, wherein the coating contains at least one of a flavoring and a coloring approved for foodstuffs.

10. The toothpick in accordance with claim 7, wherein the coating contains at least one of a pharmaceutical agent and an anti-bacterial agent.

11. The toothpick in accordance with claim 10, wherein one of the base material and the coating contains at least one of dissolved natural medicaments and dissolved medicinal plants.

12. The toothpick in accordance with claim 10, wherein one of the base material and the coating contains nicotine.

13. The toothpick in accordance with claim 1, wherein prior to processing the base material is formed as granules of a polymer.

14. The toothpick in accordance with claim 6, wherein one of the base material and the coating contains at least one of dissolved natural medicaments and dissolved medicinal plants.

15. The toothpick in accordance with claim 5, wherein one of the base material and the coating contains at least one of dissolved natural medicaments and dissolved medicinal plants.

16. The toothpick in accordance with claim 5, wherein one of the base material and the coating contains nicotine.

* * * * *